(12) United States Patent
Wallano (10) Patent No.: US 11,318,182 B1
(45) Date of Patent: May 3, 2022

(54) PLANT EXTRACT FOR SKIN INFECTIONS

(71) Applicant: Eyob Wanorie Wallano, Los Angeles, CA (US)

(72) Inventor: Eyob Wanorie Wallano, Los Angeles, CA (US)

(*) Notice: Subject to any disclaimer, the term of this patent is extended or adjusted under 35 U.S.C. 154(b) by 0 days.

(21) Appl. No.: 17/144,181

(22) Filed: Jan. 8, 2021

(51) Int. Cl.
*A61K 36/9068* (2006.01)
*A61K 36/8962* (2006.01)
*A61K 36/48* (2006.01)
*A61K 9/00* (2006.01)
*A61K 36/31* (2006.01)
*A61K 36/889* (2006.01)
*A61P 31/04* (2006.01)

(52) U.S. Cl.
CPC ........ *A61K 36/9068* (2013.01); *A61K 9/0014* (2013.01); *A61K 36/31* (2013.01); *A61K 36/48* (2013.01); *A61K 36/889* (2013.01); *A61K 36/8962* (2013.01); *A61P 31/04* (2018.01)

(58) Field of Classification Search
CPC ............ A61K 36/9068; A61K 36/8962; A61K 36/48; A61K 9/0014; A61K 36/31; A61K 36/889; A61P 31/04
See application file for complete search history.

(56) References Cited

U.S. PATENT DOCUMENTS

2013/0261183 A1* 10/2013 Bhagat .................... A61P 37/00
426/71
2019/0216765 A1* 7/2019 Rehm .................... A61K 47/44
2019/0216871 A1* 7/2019 Rehm .................... A61K 47/14

* cited by examiner

*Primary Examiner* — Aaron J Kosar
(74) *Attorney, Agent, or Firm* — Patent PC; Bao Tran (57) ABSTRACT

A method for treatment of at least one fungal infection of a mammal includes administering a composition consisting of grinded garlic, ginger, papaya seed, clover bud, tamarind and coconut oil components extracted by 95% ethanol and kept in darkness for about four days.

18 Claims, 7 Drawing Sheets

FIG. 3 *Staphylococcus aureus*

Legend:
1 & 2 plant extracts
3. Tetracycline
4. Penicillin
5. Undecycleric acid 25%
6. Clotrimazole 1%

Legend:
1 & 2 plant extracts
3. Tetracycline
4. Penicillin
5. Undecycleric acid 25%
6. Clotrimazole 1%

Legend:
1 & 2 plant extracts
3. Tetracycline
4. Penicillin
5. Undecycleric acid 25%
6. Clotrimazole 1%

*Escherichia coli*

PLANT EXTRACT FOR SKIN INFECTIONS

The present disclosure relates to a composition with all-natural ingredients for use in the treatment of fungal infections of the skin of a mammal, especially a human being, such as by topical or spray administration of the composition on the affected area.

BACKGROUND

Fungal infections are caused by fungi, which depends on the environmental organic matters. Many fungi are very dangerous to the health of humans and animals.

Fungus is a microorganism its survival depends on organic matter. Fairly small amount are parasitic (pathogenic) and prefer the living host and large group of fungi are saprophytic (nonpathogenic) which prefer dead and decayed materials. Among the pathogenic fungi several of them cause lower respiratory diseases and a few of pathogenic fungi also occupy moist skin surfaces such as between toes, body skin and skin folds including the foot pads. Abundantly, the mold and yeast are categorized to cause skin infections known to be Tinea pedum, Tinea pedis, Moccasin foot and ringworm. The importance of antifungal drugs has been increased dramatically since fungal diseases frequently occur on superficial surfaces such as skin, skin structures and mucosa. In general, fungal infections cause serious problem human health resulting in significant number of morbidity and mortality and increasingly recognized as an emerging threat to public health. Current epidemiological data shows that incidence and prevalence rates of fungal infections of the skin are on the rise and many of these fungi evolve resistance to drugs.

The increased use of antifungal agents has caused resistance which may lead to an increase of the fungal diseases globally. It is believed that the incidence of clinical yeast infections increased due to the extensive use of broad-spectrum antifungal agents which proportionally increased the drug resistance. Additionally, a lack of variation in antifungal medications, high doses of these medications occasionally contribute to patients' toxicity, and in part contribute to the high morbidity and mortality.

SUMMARY

The above drawbacks and deficiencies of the prior art are overcome or alleviated by, in a first aspect, a composition comprising all natural ingredients for use in the treatment of fungal infections of mammals.

In one aspect, a method for treatment of at least one fungal infection of a mammal includes administering a composition consisting of grinded garlic, ginger, papaya seed, clover bud, tamarind and coconut oil components extracted by 95% ethanol and kept in darkness for about four days.

In another aspect, a combination of plant extracts is provided as an alternative treatment for fungal and bacterial infections. The plant extracts include garlic bulb, ginger stem, papaya seed, clover bud, tamarind fruits, coconut oil were extracted by 95% ethanol. A drop of peppermint oil, 1% citric acid and 1% NaCl added to the final crude extract and tested for the efficacy against a group of fungal and bacterial species. The fungal species may be selected from one of: *Serratia marcescens, Penicillium notatum*, and *Aspergillus niger*, while the bacterial species were comprised of *Escherichia coli, Bacillus cereus* and *Staphylococcus aureus*.

Results from trials showed that the combination of the plant extracts have high growth inhibitory activity with minimum or no side effects compared to commercially available products such as undecylenic acid 25% or clotrimazole 1%. Antibiotics such as Penicillin and Tetracycline included in the study. In vivo trial, 25 of the 28 tested human subjects showed fungal clearance within a week of using the plant extract of 29 μg on the affected site twice daily. This natural product may be considered as an alternative new treatment for fungal and few antibacterial skin infections. However, further study of safety, efficacy, and synergism of each plant is necessary to enlighten their uses in the future.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION

According to the epidemiological data, the incidence and prevalence of fungal infections of the skin, and the increasing of antifungal agents' occurrence creates resistance to the drugs. To alter this resistance, certain research approached to increase the efficacy of antifungals drugs combing with medically known plants extract in the form of natural extracts as a single or combined.

The product is fully natural without any side effects, but as individual skin sensitivity differs from person to person, the user should consult a physician to resolve the issues. The product is fully formulated from plant extracts as microbiocidal designed to control the skin mold, yeast and bacterial infections with the effect and safety. The key ingredients to combat the skin infections are all natural and listed below:

1. Garlic—microbicide effect, anti-inflammatory property
2. Coconut oil—moisturizes skin, serves as topical antifungal and antibacterial property
3. Ginger—anti-inflammatory and microbicidal property
4. Papaya seed—antifungal and has effect on skin care, moisturizes and improves skin elasticity. Heals scars, burns, and skin diseases (Ringworm).
5. Clove buds—swerve as antiseptic and analgesic property.
6. Tamarind—anti-inflammatory and wound healing properties
7. Citric acid—kills bacteria, mold, mildew and used as preservative.
8. Sodium chloride—preservatives and antiseptics.

9. Peppermint—relieves pain beneath the skin and flavoring agent

Materials and Method.

1. Grinded garlic+95% Ethanol, mixed and kept in dark for 10-30 days at room temperature and then refrigerated at +4 degree centigrade.
2. Grinded ginger+95% Ethanol, mixed and kept in dark for 10-30 days at room temperature, and then refrigerated at +4 degree centigrade.
3. Grinded papaya seed+95% Ethanol, mixed and kept in dark for 10-30 days at room temperature and then refrigerated at +4 degree centigrade.
4. Clover buds+95% Ethanol, mixed and kept in dark for 10-30 days at room temperature and then refrigerated at +4 degree centigrade.
5. Coconut oil+95% Ethanol, mixed and kept in dark for 10-30 days at room temperature and then refrigerated at +4 degree centigrade.
6. Tamarind+95% Ethanol, mixed and kept in dark for 10-30 days at room temperature.

Use of product and its application is detailed next. The product is principally formulated and tested its sensitivity to inhibit the growth and clinically to control the skin fungal and bacterial infections. It is recommended that the product not be used near the eyes, mouth, and nostrils and not to taken by mouth. If any contact on those sites, wash with abundant water to be in safe side. The infection clearance from the skin depends on individual's health condition and skin sensitivity to the product. The plant extract can be used in a spray category in 20 ml or 30 ml spray bottles.

In the preferred embodiment, grinded garlic, ginger, papaya seed, clover bud, tamarind and the coconut oil components are extracted by 95% ethanol and kept in dark four days at room temperature. The extracted homogenous texture is filtered through Whatman filter paper no. 1 by using Thermo Scientific Vacuum USA. The filtered extract pH is adjusted to 5.6. A drop of Lavender is added to the final concentration and the extract is refrigerated in sealed, amber-colored bottles at 4° C. after the concentration is determined. The extract is used to test microbicidal activity using penicillin, tetracycline, commercialized liquid antifungal agents as clotrimazole 1% and undecylenic acid 25%. *Serratia marcescens*, *Penicillium notatum*, and *Aspergillus niger* used as fungal species. Known isolates of *Escherichia coli*, *Bacillus serous* and *Staphylococcus aureus* used as bacterial species. Sabouraud dextrose agar (SDA) medium and Nutrient agar plates (NAP) used to confirm in vitro inhibition of the fungus and bacteria in 24, 48 and 72 hours at room temperature and 37° C. respectively. The antimicrobial activity of plant-extract specified by the formation of an inhibition zone is measured by using Vernier calipers. Also, 28 individuals evaluated after using the mixed plant-extract within two weeks trial controlling fungal and bacterial infections of the skin.

Figure 1:
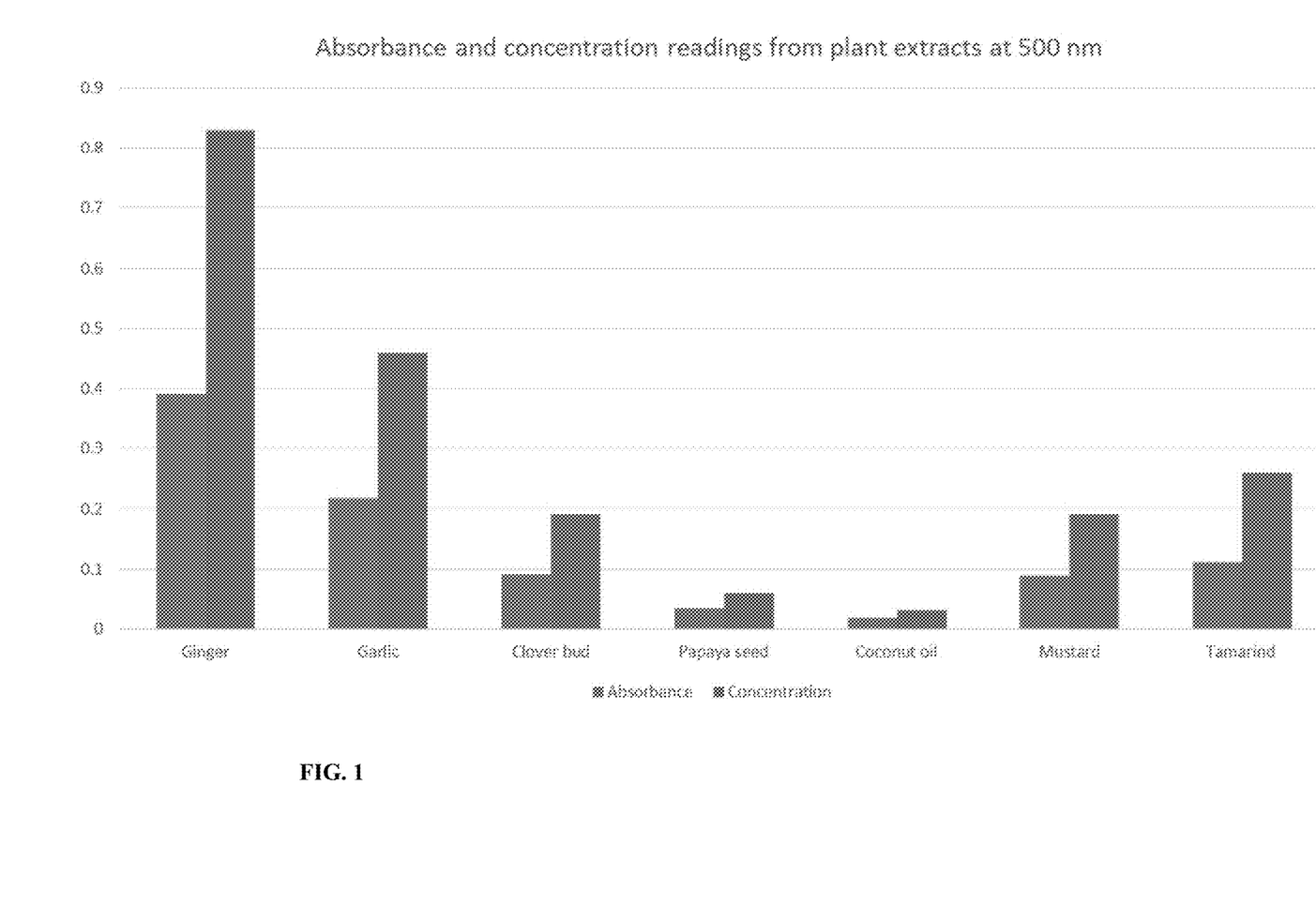
FIG. 1 is a chart illustrating exemplary absorbance and concentration of the extracts.
Figure 2:
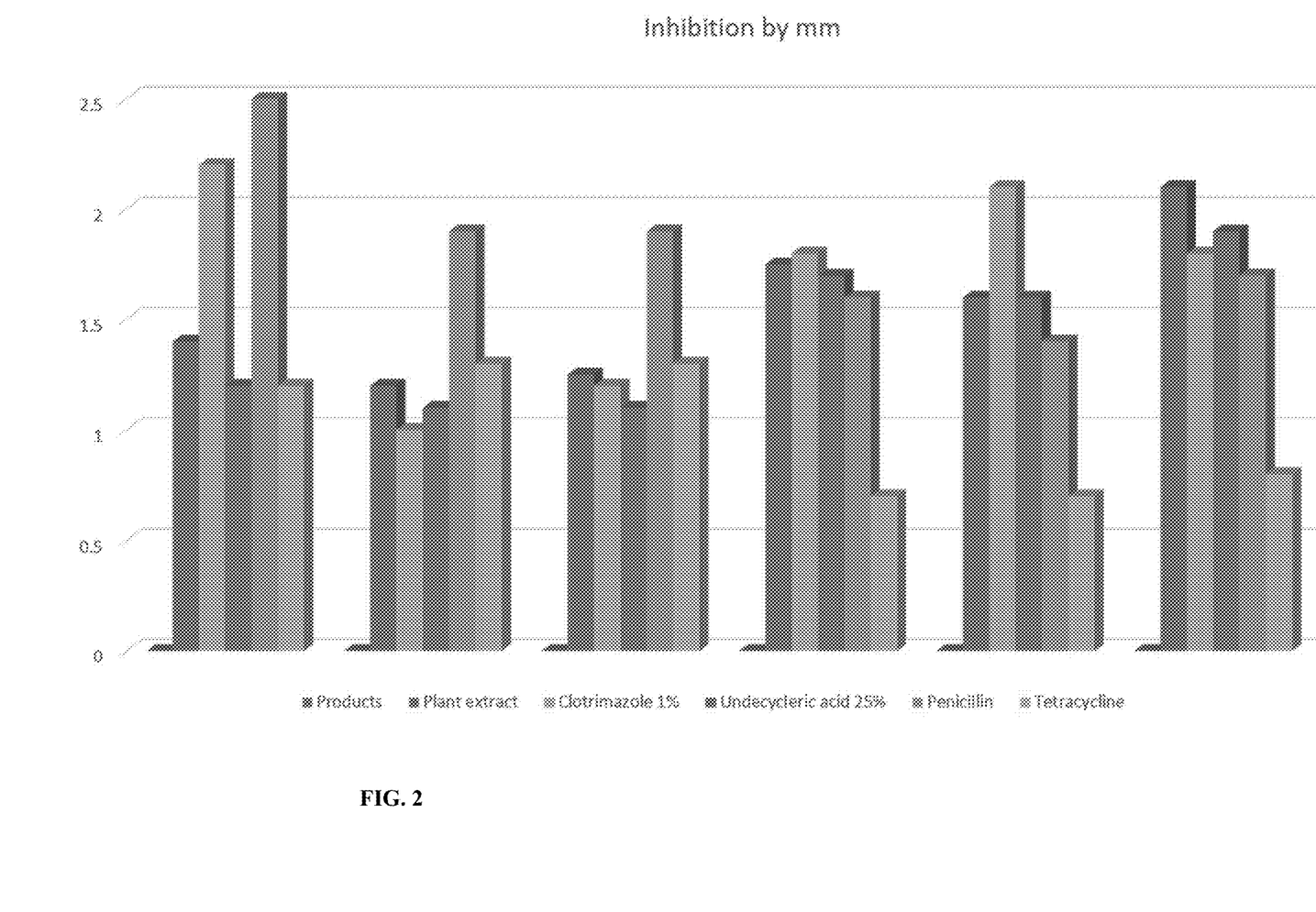
FIG. 2 shows exemplary growth inhibition effects of the inventive solutions.
Figure 3:
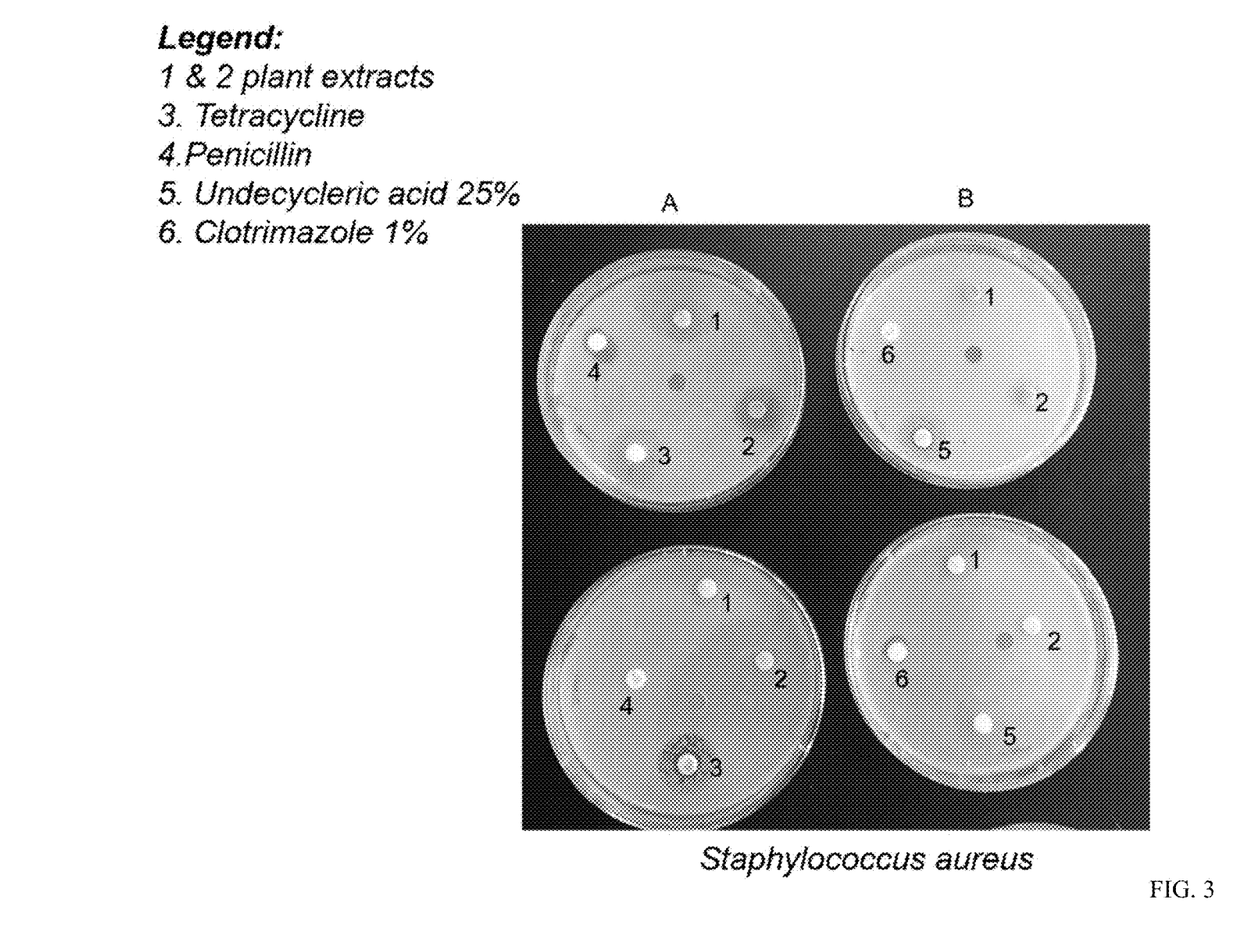
FIG. 3 shows exemplary inhibition test on *Staphylococcus aureus*.
Figure 4:
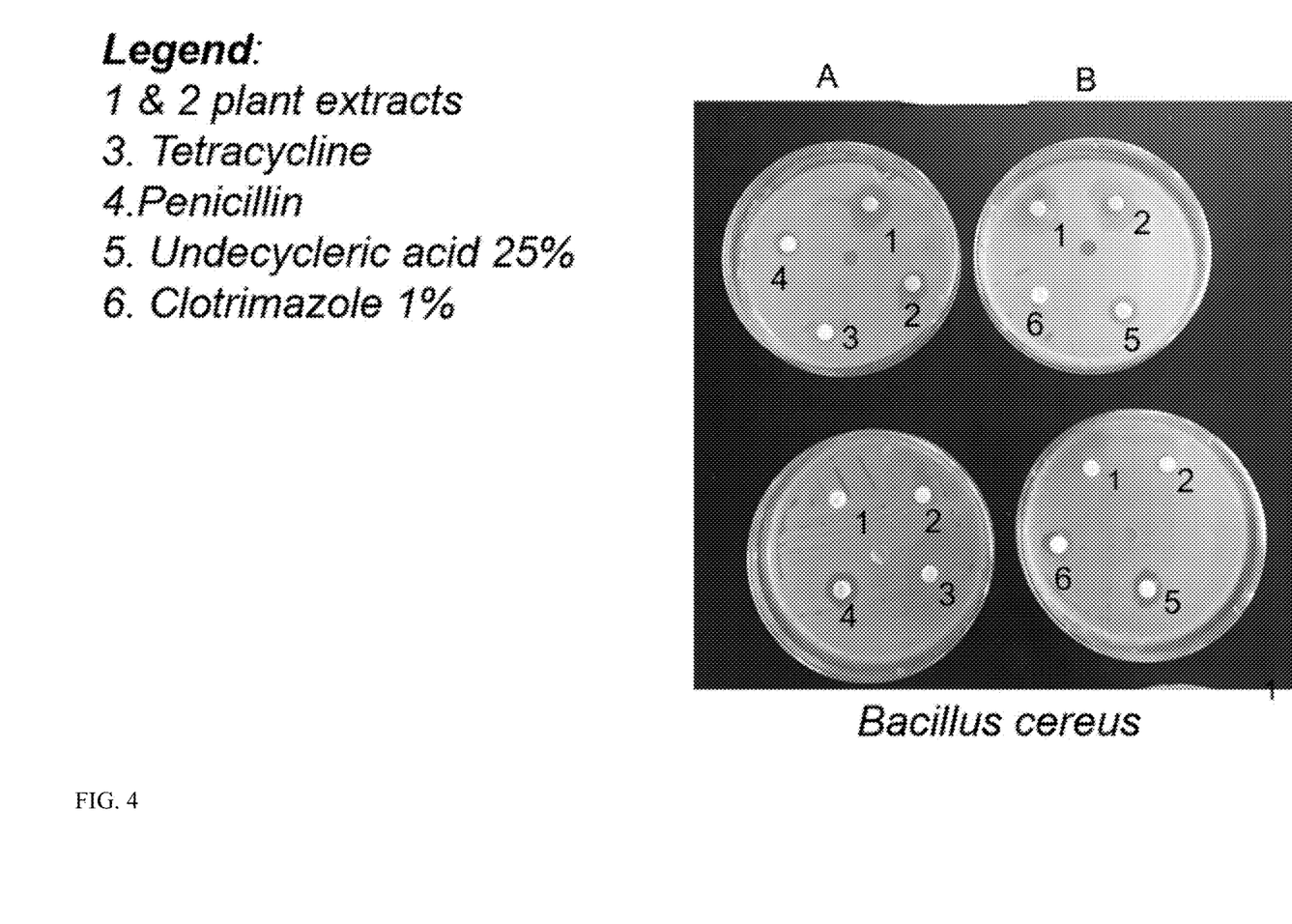
FIG. 4 shows exemplary inhibition test on *Bacillus cereus*
Figure 5:
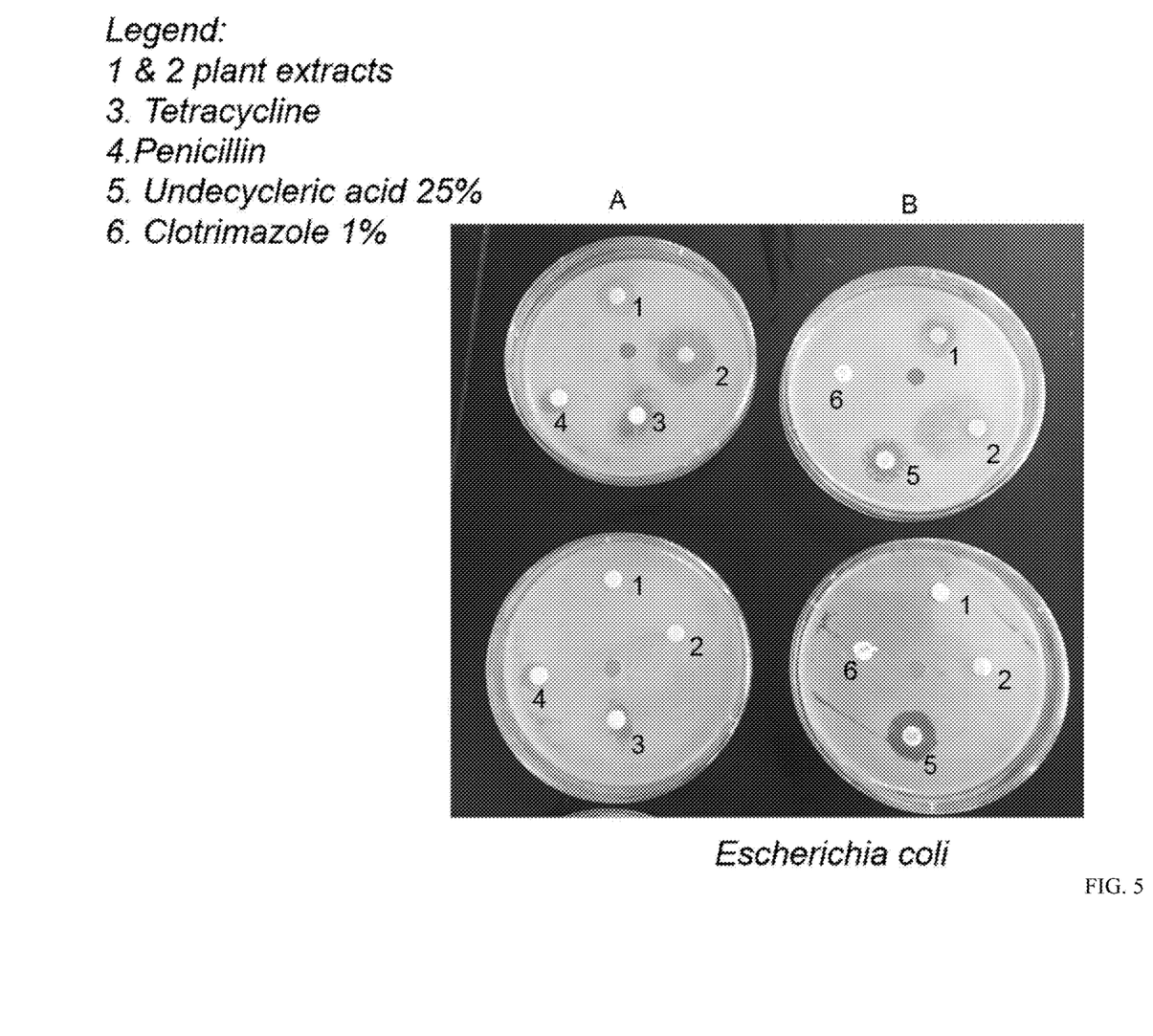
FIG. 5 shows exemplary inhibition test on *Escherichia coli*.

In another embodiment, plant-derived antibacterial and antifungals of skin can be formed from ginger root, garlic root, clover bud, tamarind fruit, papaya seed, and coconut oil where crude extract performed by 95% ethanol keeping the mixture for four days refrigerated at 4° C. The crude is extracted using one mm Whatman filter by Thermo Scientific Vacuum to reach as a combined 29 µg/ml crude extract (FIG. 1). The crude extracts exhibit high concentration on ginger, garlic, papaya seed, clover bud and the lowest concentration was with coconut oil next to tamarind fruit. The mixture of those plants as combined 29 µg/ml tested to prevent the growth of fungi. *Staphylococcus aureus*, *Bacillus cereus* and *Escherichia coli* as bacterial species were also tested with the crude plant extract as certain component of fungi and bacteria exhibit the various practical relevance of interactions physically and metabolically.

All the extracts evaluated were found to have variable inhibitory activities on bacterial and fungal species listed. *Staphylococcus aureus*, *Bacillus cereus* and *Escherichia coli* grown on nutrient agar (NA). *Aspergillus niger*, *Penicillium notatum* and *Serratia marcescens* tested fungal species grown on Sabouraud dextrose agar (SDA). The potency of the crude extract was tested for minimum growth inhibition (MGI) compared to commercially available liquid antifungals (Clotrimazole 1% and Undecylenic acid 25%), and antibiotics (Tetracycline and Penicillin). The SDA and NA plates were filled with 20 ml of media and solidified in 24 hours at 37° C. incubator before inoculation of the of the microorganisms and the products to be tested.

TABLE 1

| | Growth inhibition by mm | | | | | |
|---|---|---|---|---|---|---|
| Products | E. coli | B. cereus | S. Aureus | S. marcescens | P. notatum | A. niger |
| Plant extract | 1.4 | 1.2 | 1.25 | 1.75 | 1.6 | 2.1 |
| Clotrimazole 1% | 2.2 | 1 | 1.2 | 1.8 | 2.1 | 1.8 |
| Undecyleric add 25% | 1.2 | 1.1 | 1.1 | 1.7 | 1.6 | 1.9 |
| Penicillin | 2.5 | 1.9 | 1.9 | 1.6 | 1.4 | 1.7 |
| Tetracycline | 1.2 | 1.3 | 1.3 | 0.7 | 0.7 | 0.8 |

Figure 6:
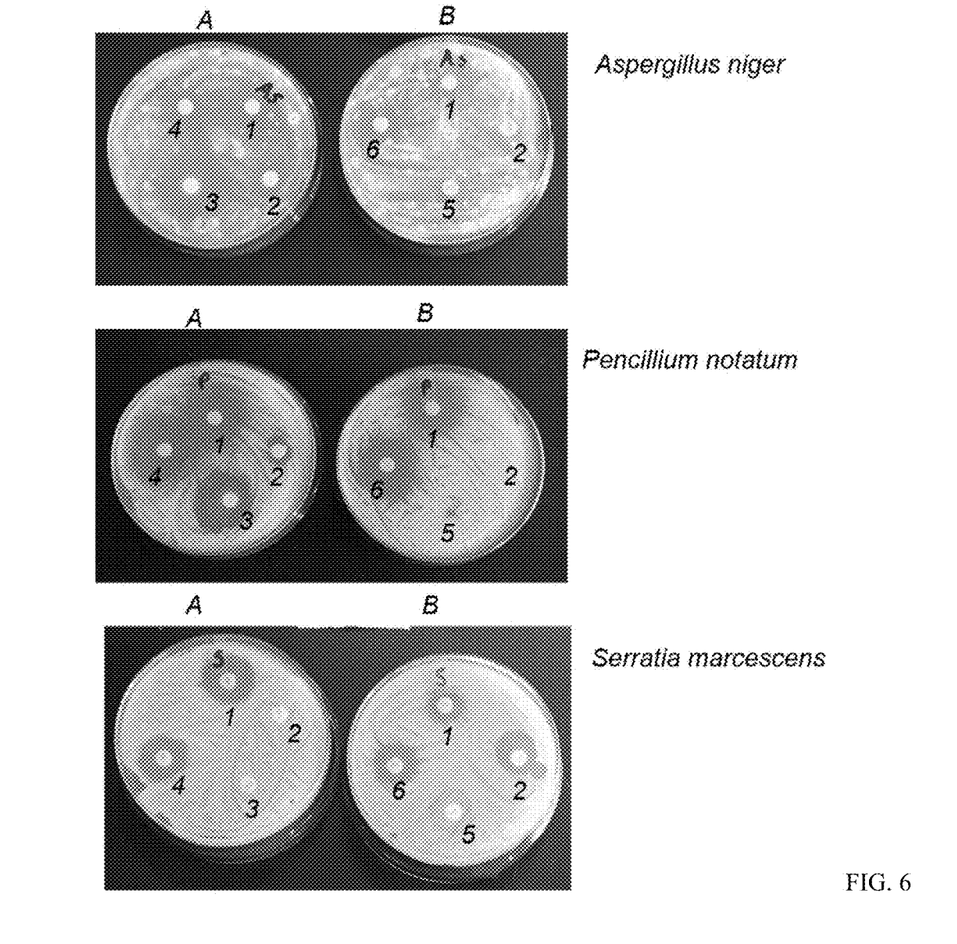
FIG. 6 shows exemplary inhibition test on fungi.

The MGI on Table 1 and FIGS. 2, 3, 4 and 5 show that similar growth inhibitory activity observed among our plant extract, commercially available clotrimazole 1% and undecylenic acid 25%. Penicillin exhibits higher MGI than tetracycline on tested against fungi and bacteria. The products tested on the three fungi with the plant-derived extracts, commercially available liquid drugs and the two antibiotics show variable inhibitory effect (FIG. 6) whereas our crude extract of 29 µg/ml exhibits similar and higher fungi inhibiting activity as reflected on Table one on in vitro trial. Our plant-derived extract is a promising strategy research comparing to antibacterial may help to progress toward developing effective antimicrobials against skin infections.

Figure 7:
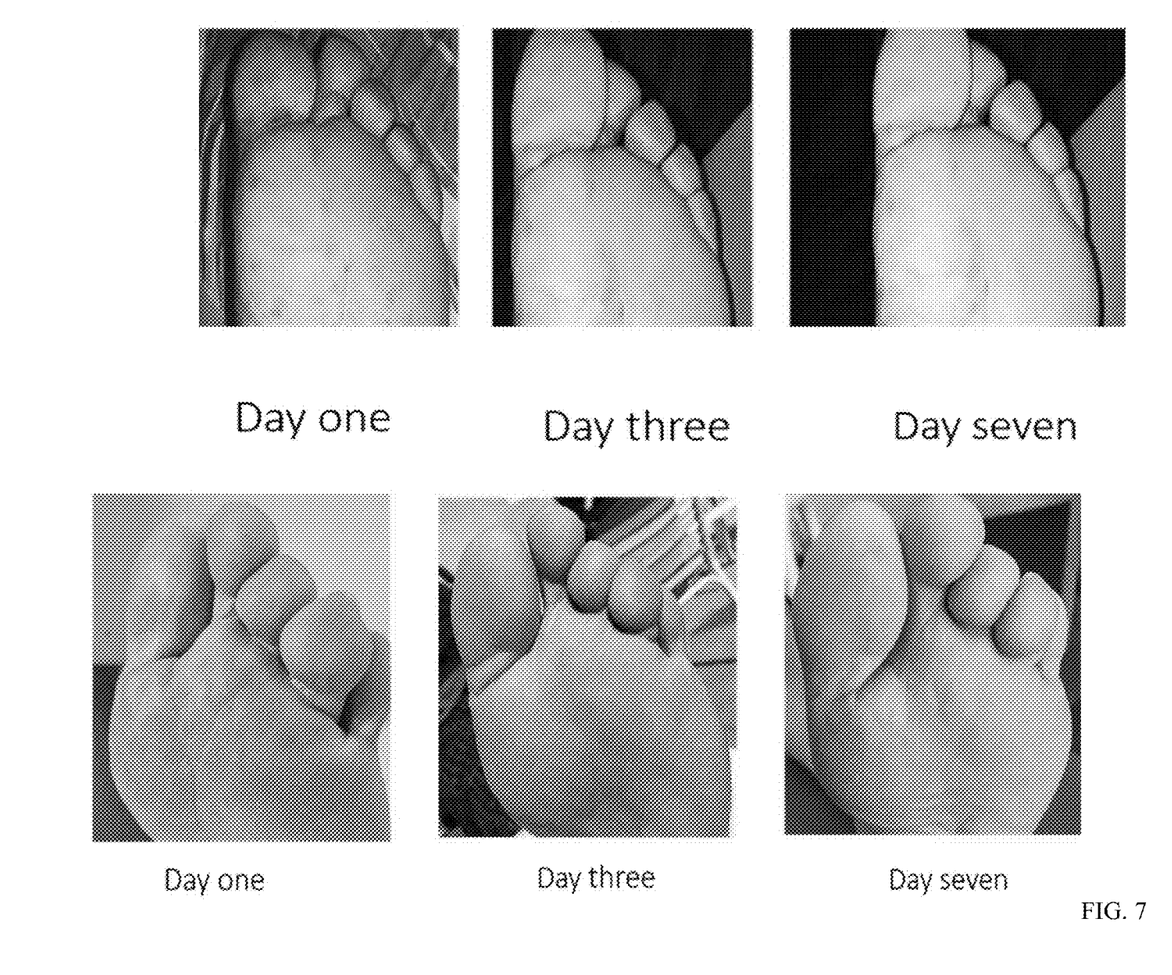
FIG. 7 shows an exemplary trial on feet.

The crude extract of spray tried in vivo on 28 individuals who clinically found to have foot fungal infections and the result clinically observed within a week by two times application in vivo trial, 25 out of 28 (80%) of individuals' foot infection exhibited the best result of fungal clearance at the end of the week (FIG. 7).

Treatment with the composition is painless and has not shown any side-effects, not even after long term use. The effect of the treatment can be maximized. Thus, the composition can be used as one of the following coatings: ointments, lotions, suspensions, gels, sprays or in other topical carriers suitable for the treatment, whereby in this context conventional carriers and optional additives are used.

Topical administration may for example be achieved by painting or through the use of a cotton pad stick or spray. The composition may for example be administered topically onto the affected area twice daily for a week for as long as required, i.e. until no sign of infection can be detected. Typically, the treatment may be repeated after from 10 to 12 weeks. In severe cases, the treatment may be repeated several times a week, but this is generally not needed for achieving a good and effective treatment. If the patient is a human being, he or she can treat him- or herself, which makes the treatment both quick and easy.

In sum, a combination of plant-extracts efficiently inhibits most of the fungal and bacterial infections of the skin. To overcome these challenges, our conducted research of plant-derived extract is a tool to treat skin fungal infections in sustainable, affordable and with effective activity. Our developed plant-extract is focused on treating the most fungal and bacterial infections of the skin. The extract is produced as organic antifungal spray, cream, or powdered form. The product brands can be used for human and animal superficial fungal and bacterial infections.

It is to be understood that these various percentages may vary slightly and still yield a viable anti-fungal composition of the present invention. Various other agents, such as beeswax and aloe vera, may be added to the cream version of the composition as hardening agents, if desired.

In addition, the composition to be used in the method may optionally be used with a lubricant, such as an oil, including, but not limited to, anise oil, bay oil, bergamot oil, borage oil, canola oil, castor oil, cedar oil, cinnamon oil, lard oil, clove oil, coconut oil, corn oil, macadamia nut oil, linseed oil, olive oil, palm oil, peanut oil, sunflower seed oil, soybean oil, sesame oil, avocado oil, basil oil, almond oil, birch oil, cardamom oil, chamomile oil, eucalyptus oil, ginger oil, lemon oil, lavender oil, lime oil, mandarin oil, orange oil, rose oil, rosemary oil and apple oil. Typically, lemon oil or apple oil is used, however, it is to be understood that any oil or other substance providing a lubricating effect may be used. Further, said lubricant may represent a pharmaceutically acceptable lubricant.

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. A method for treatment of at least one fungal infection of a mammal, comprising:
    administering a composition consisting of grinded garlic, ginger, papaya seed, clover bud, tamarind and coconut oil components extracted by 95% ethanol and kept in darkness for about four days.

2. The method according to claim 1, wherein said method is for treatment of at least one fungal infection of the foot or nail.

3. The method according to claim 1, wherein said method is for treatment of at least one fungal infection of the skin.

4. The method according to claim 3, wherein the at least one fungal infection of the skin represent Athlete's foot.

5. The method according to claim 1, comprising mixing grinded garlic extracted by 95% ethanol and kept in dark for 10-30 days at room temperature and then refrigerated at +4 degree centigrade.

6. The method according to claim 1, comprising mixing grinded ginger extracted by 95% ethanol and kept in dark for 10-30 days at room temperature and then refrigerated at +4 degree centigrade.

7. The method according to claim 1, comprising mixing grinded papaya seed extracted by 95% ethanol and kept in dark for 10-30 days at room temperature and then refrigerated at +4 degree centigrade.

8. The method according to claim 1, comprising mixing grinded clover buds extracted by 95% ethanol and kept in dark for 10-30 days at room temperature and then refrigerated at +4 degree centigrade.

9. The method according to claim 1, comprising mixing coconut oil extracted by 95% ethanol and kept in dark for 10-30 days at room temperature and then refrigerated at +4 degree centigrade.

10. The method according to claim 1, comprising mixing grinded tamarind extracted by 95% ethanol and kept in dark for 10-30 days at room temperature and then refrigerated at +4 degree centigrade.

11. The method according to claim 1, wherein the composition is topically administered onto an affected area.

12. The method according to claim 11, wherein the composition is topically administered onto the affected area once a week.

13. The method according to claim 1, wherein the composition is administered to the skin and/or nail(s) by painting or spraying.

14. The method according to claim 1, wherein the mammal is a human.

15. The method according to claim 1, comprising filtering the components.

16. The method according to claim 1, comprising adjusting the pH to about 5.6.

17. The method according to claim 1, comprising adding peppermint oil, 1% citric acid and 1% sodium chloride.

18. The method according to claim 1, wherein the composition is topically administered for one to two weeks.

* * * * *